US012279967B2

(12) United States Patent
Halverson et al.

(10) Patent No.: US 12,279,967 B2
(45) Date of Patent: Apr. 22, 2025

(54) POROUS INTERBODY SPACER

(71) Applicant: Nexus Spine, L.L.C., Salt Lake City, UT (US)

(72) Inventors: Peter Halverson, Draper, UT (US); David Hawkes, Pleasant Grove, UT (US)

(73) Assignee: NEXUS SPINE, LLC, Salt Lake City, UT (US)

(*) Notice: Subject to any disclaimer, the term of this patent is extended or adjusted under 35 U.S.C. 154(b) by 0 days.

(21) Appl. No.: 15/372,290

(22) Filed: Dec. 7, 2016

(65) Prior Publication Data
US 2017/0156880 A1 Jun. 8, 2017

Related U.S. Application Data

(60) Provisional application No. 62/264,217, filed on Dec. 7, 2015, provisional application No. 62/355,789, filed on Jun. 28, 2016.

(51) Int. Cl.
| | | |
|---|---|---|
| A61F 2/30 | (2006.01) | |
| A61F 2/00 | (2006.01) | |
| A61F 2/44 | (2006.01) | |

(52) U.S. Cl.
CPC .......... *A61F 2/447* (2013.01); *A61F 2/0077* (2013.01); *A61F 2/4455* (2013.01);
(Continued)

(58) Field of Classification Search
CPC .................. A61F 2/442; A61F 2002/4415
See application file for complete search history.

(56) References Cited

U.S. PATENT DOCUMENTS 3,867,728 A * 2/1975 Stubstad ............. A61F 2/30907
128/DIG. 21
4,309,777 A 1/1982 Patil
(Continued)

FOREIGN PATENT DOCUMENTS

| WO | 2011143219 A1 | 11/2011 |
|---|---|---|
| WO | 2016130878 A1 | 8/2016 |

OTHER PUBLICATIONS

International Search Report from corresponding PCT case.
(Continued)

*Primary Examiner* — Nicholas W Woodall
(74) *Attorney, Agent, or Firm* — Bryant J. Keller; Kirton McConkie

(57) ABSTRACT

Orthopedic implants, particularly interbody spacers, have a combination of correct pore size and stiffness/flexibility. When the implants have the proper pore size and stiffness, osteocytes are able to properly bridge the pores of the implant and then experience a proper compressive load to stimulate the bone cells to form bone within the pores. An implant includes a body formed of an osteoconductive material and having a stiffness of between 400 megapascals (MPa) and 1,200 MPa. Additionally, the body includes a plurality of pores having an average size of between 150 microns and 600 microns. The pores permit the growth of bone therein. The body is formed of packs of coils which may be formed using an additive manufacturing process and using traditional orthopedic implant materials such as titanium and titanium alloys while still achieving desired stiffness and pore sizes of the implants.

20 Claims, 7 Drawing Sheets

(52) U.S. Cl.
CPC ............... *A61F 2002/0081* (2013.01); *A61F 2002/30146* (2013.01); *A61F 2002/30149* (2013.01); *A61F 2002/30153* (2013.01); *A61F 2002/30154* (2013.01); *A61F 2002/30289* (2013.01); *A61F 2002/30566* (2013.01); *A61F 2002/30568* (2013.01); *A61F 2002/30593* (2013.01); *A61F 2002/30784* (2013.01); *A61F 2002/3092* (2013.01); *A61F 2002/3093* (2013.01); *A61F 2002/3097* (2013.01); *A61F 2002/4495* (2013.01); *A61F 2310/00023* (2013.01); *A61F 2310/00131* (2013.01)

(56) References Cited

U.S. PATENT DOCUMENTS

| | | | | |
|---|---|---|---|---|
| 7,309,357 | B2* | 12/2007 | Kim | A61F 2/442 623/17.13 |
| 7,517,228 | B2* | 4/2009 | Baskaran | H05K 1/147 439/67 |
| 7,575,598 | B2* | 8/2009 | Albert | A61F 2/442 623/17.13 |
| 7,604,870 | B2 | 10/2009 | Chernyshov et al. | |
| 7,892,285 | B2* | 2/2011 | Viker | A61F 2/4611 623/17.13 |
| 8,303,662 | B2 | 11/2012 | Landry et al. | |
| 9,314,337 | B2 | 4/2016 | Patterson et al. | |
| 9,918,849 | B2* | 3/2018 | Morris | A61F 2/30744 |
| 10,660,763 | B2 | 5/2020 | Wilson et al. | |
| 2001/0039456 | A1* | 11/2001 | Boyer, II | A61F 2/44 623/23.52 |
| 2001/0051829 | A1 | 12/2001 | Middleton | |
| 2002/0128714 | A1* | 9/2002 | Manasas | A61F 2/442 623/17.15 |
| 2005/0112397 | A1 | 5/2005 | Rolfe et al. | |
| 2006/0041262 | A1* | 2/2006 | Calvert | A61F 2/28 606/76 |
| 2006/0052872 | A1* | 3/2006 | Studer | A61F 2/4425 623/17.13 |
| 2006/0241763 | A1* | 10/2006 | Paul | A61F 2/44 623/17.11 |
| 2008/0147098 | A1 | 6/2008 | Trieu | |
| 2009/0143867 | A1* | 6/2009 | Gage | A61L 27/56 623/23.72 |
| 2010/0137990 | A1* | 6/2010 | Apatsidis | A61F 2/4425 623/17.16 |
| 2011/0029087 | A1 | 2/2011 | Haider et al. | |
| 2012/0016480 | A1 | 1/2012 | Gerber et al. | |
| 2017/0143502 | A1* | 5/2017 | Yadin | A61F 2/442 |
| 2017/0216036 | A1* | 8/2017 | Cordaro | A61B 50/30 |

OTHER PUBLICATIONS

Supplementary European Search Report and European search opinion from corresponding European case.
InFix Anterior Lumbar Device, Surgical Technique Guide, Zimmer Biomet Spine, Inc., 2018.

* cited by examiner

POROUS INTERBODY SPACER

CROSS-REFERENCE TO RELATED APPLICATIONS

This application claims the benefit of U.S. Provisional Application No. 62/264,217, filed Dec. 7, 2015, and U.S. Provisional Application No. 62/355,789, filed Jun. 28, 2016, each of which is incorporated by reference herein for all it discloses.

BACKGROUND OF THE INVENTION

1. Field of the Invention

The present invention relates to spinal fusion implants, and more particularly to a porous interbody spacer having advantageous properties to facilitate support and bone growth into the implant.

2. Background and Related Art

Human bones are generally formed of two types of structural bone tissue: cortical bone and trabecular or cancellous bone. Cortical bone generally forms the outer shell of most bones, and is more dense, harder, stronger, and stiffer than trabecular bone. Trabecular bone is typically found at the ends of long bones proximal to joints, as well as in the interior of vertebrae. Trabecular bone is highly vascularized and has a generally porous or spongy structure through which blood vessels pass. Generally, trabecular bone has pores that are on the order of 150 to 650 microns in size. Not all trabecular bone has the same porosity: different bones have different trabecular bone porosity.

The physical characteristics of bone are important for physiological purposes related to the growth and formation of bone both originally as well as during the healing process. The cells responsible for bone growth, including osteocytes and osteoblasts, work together to form bone as needed within the body, but will only form bone under proper conditions, including when the cells experience proper loads and stresses, when a network of blood vessels is available to supply needed nutrients, and when gaps to be filled by bone are of a proper size. When proper conditions are not available, bone cannot or will not grow. For example, when bone does not experience loading, it will not grow and can even be resorbed. Additionally, when gaps to be filled are too large or too small, bone cannot bridge the gap and will not grow.

In addition to proper physical conditions, bone growth only occurs when certain conditions are met. First, there must be a kernel of living bone to start the process. The living bone supplies the cells necessary for bone growth and formation. Additionally, a cascade of chemical triggers is required for bone to grow. Finally, because bone growth is impeded by the presence of certain materials and/or chemicals, an absence of such materials and chemicals is required for proper bone growth.

One example of where it is generally recognized as advantageous to promote bone growth is in the orthopedic implant industry. One goal with many orthopedic implants is for bone growth at the interface to fuse or secure the implant to the bone. For this reason, many orthopedic implants are provided with a porous surface at the bone-implant interface, with the expectation that bone will grow into the porous surface of the implant. Other implants may be provided with one or more cavities or voids to receive bone growth (e.g., a graft window), and during surgery any such cavities or voids may be filled with a material intended to promote bone growth, including morcellized bone graft material. These techniques have been used in implants for years with varying degrees of success, but the success of such devices has been limited by the devices' ongoing failure to provide physical and chemical characteristics most conducive to bone growth. Even when a graft is present in a cavity or void, any bone that does form on or around the device is of lesser quality and quantity.

Generally, current implants have one or more characteristics that are not maximally conducive to facilitating bone growth into the implant. For example, some implants may provide a pore size that is generally within a desirable range, but may have a stiffness that is too high to allow bone within the porous structure of the implant to be properly loaded. As a result, the bone will not take advantage of the correct porosity and pore size of such implants, and will grow only minimally, if at all, in the porous structure of such implants. In other implants, the stiffness may be generally within a desirable range, but in order to achieve the desired stiffness, the device manufacturer creates pores that are too large or too small to facilitate proper bone growth. As a result, while the bone cells can be properly loaded, they are unable to grow bone in the available pores.

Some manufacturers have used the material polyetheretherketone (PEEK) in orthopedic implants, as PEEK has a bulk stiffness (4 gigapascals (GPa)) that is close to that of bone (0.3 GPa<bone stiffness <4 GPa). Unfortunately, PEEK is not chemically a bone-friendly material. As a result, when PEEK is used for implants, a fibrous layer is formed by the body around the implant to protect the body from the PEEK, and bone growth does not occur. Other commonly used materials are titanium and tantalum, which are osteoconductive but have a relatively high bulk stiffness (approximately 116 GPa) that shields the bone from appropriate mechanical stimulus necessary for proper bone growth. Stainless steel, another possible implant material, is not very osteoconductive and also has a very high bulk stiffness (approximately 210 GPa).

Many currently available implants made of titanium have a stiffness that approaches the stiffness of a block of solid titanium. These devices are typically too stiff even in their porous regions. Additionally, many devices have porous regions contained within a solid surrounding structure that prevents the intervening porous region from being loaded in a way conducive to bone growth. Trabecular metal is one of the least stiff predicate materials that is still more than twice as stiff as the maximum desired stiffness desired to promote bone growth through proper loading.

One particular type of implant that is illustrative of the difficulties encountered with predicate devices is an interbody spacer intended for placement between vertebral bodies in spinal fusion procedures. Predicate devices have focused almost exclusively on providing support for the spine, giving little to no attention to promoting or stimulating bone growth. As a result, while such devices may achieve bone on-growth at the surface of the device, such devices do not achieve ingrowth that extends throughout the devices.

For example, the TM-S® cervical fusion device and the TM Ardis® interbody system by Zimmer Biomet are made using elemental tantalum ("trabecular metal") and achieve a pore size on the order of 550 microns. Despite having a pore size that is generally within the desired range, the stiffness of the implant is determined by the size and shape of the material between the pores, and remains at least twice and as much as ten times the desired stiffness. Due to the lack of proper loading, bone does not grow within the Zimmer devices to a significant extent.

Similarly, Stryker's Tritanium® PL posterior lumbar cage has a pore size of 616 microns, only slightly exceeding the desired pore size. Again, however, the device's stiffness is determined by the size and shape of the material between the pores and at the margins of the device itself. As a result, any bone that does enter the pores of the device cannot be properly loaded, and ingrowth does not occur. The stiffness of the Stryker device may exceed the stiffness of the Zimmer devices.

Other devices, such as the 4WEB® Medical Spine Truss system, the K2M Cascadia™ devices, the Titan Endoskeleton® TO device, and the Signus-Mobis® II ST devices all have even larger pore sizes as well as portions of solid non-porous titanium along leading and trailing edges of the devices. Thus, even if portions of such devices have a stiffness that is generally correct, such portions cannot be loaded due to the solid portions of the devices. The lack of loading prevents bone growth in the interior of the devices. Additionally, the large pore sizes (e.g., on the order of greater than 1700 microns) cannot be bridged by bone.

Thus, there remains an unmet need in the orthopedic implant industry for implants that provide stiffness and pore sizes that are conducive to bone growth using materials that are also conducive to bone growth. This need is especially felt in the spinal implant industry, for example with respect to interbody spacers.

BRIEF SUMMARY OF THE INVENTION

Implementation of the invention provides orthopedic implants, particularly interbody spacers, having a combination of correct pore size and stiffness/flexibility and also provides methods for producing such orthopedic implants. When the implants have the proper pore size and stiffness, osteocytes are able to properly bridge the pores of the implant and then experience a proper compressive load to stimulate the bone cells to form bone within the pores throughout the implants according to Wolff's law.

According to implementations of the invention, an implant includes a body formed of an osteoconductive material. The body may have a stiffness of between 400 megapascals (MPa) and 1,200 MPa. Additionally, the body may include a plurality of pores having an average size of between 150 microns and 600 microns. The pores may be interconnected and permit the growth of bone therein. The implant may be an interbody spacer.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain implementations, the implant has a stiffness of between 600 MPa and 1,000 MPa. In other implementations, the implant has a stiffness of between 750 MPa and 850 MPa. In still other implementations, the implant has a stiffness of between 950 MPa and 1,050 MPa. In additional implementations, the implant has a stiffness of between 750 MPa and 1,050 MPa.

The implant may be manufactured using an additive manufacturing process. The implant may have a coil spring construction. The coil spring construction may have a vertical spacing between coils of between 250 microns and 350 microns. The coil spring construction may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate implementations of the invention, an implant includes a body comprising a plurality of coil springs formed of an osteoconductive material. The body may have a stiffness of between 400 MPa and 1,200 MPa. The body may also include a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain implementations, the implant has a stiffness of between 600 MPa and 1,000 MPa. In other implementations, the implant has a stiffness of between 750 MPa and 850 MPa. In still other implementations, the implant has a stiffness of between 950 MPa and 1,050 MPa. In additional implementations, the implant has a stiffness of between 750 MPa and 1,050 MPa.

The implant may be manufactured using an additive manufacturing process. The coil springs of the body may have a vertical spacing between coils of between 250 microns and 350 microns. The coil springs of the body may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate implementations of the invention, an implant includes a body comprising a plurality of coil springs manufactured using an additive manufacturing process. The coil springs may be arranged into a plurality of overlapping coil packs having coils that are connected and coils that are intertwined without connecting. The coil springs may include coils having a clockwise sweep direction and coils having a counterclockwise sweep direction. The body may have a stiffness of between 400 MPa and 1,200 MPa. The body may have a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain implementations, the implant has a stiffness of between 600 MPa and 1,000 MPa. In other implementations, the implant has a stiffness of between 750 MPa and 850 MPa. In still other implementations, the implant has a stiffness of between 950 MPa and 1,050 MPa. In additional implementations, the implant has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

According to further implementations of the invention, a method of manufacturing an implant includes a step of forming an implant body using an additive manufacturing process. The step of forming an implant body may include forming a plurality of coils of an osteoconductive material. The coils so formed may have a vertical coil spacing and a coil diameter chosen to impart certain physical characteristics to the implant while facilitating use of the additive manufacturing process. The implant body so formed may have a stiffness of between 400 MPa and 1,200 MPa, and may include a plurality of pores having an average size of between 150 microns and 600 microns.

In certain implementations, the implant body so formed has a stiffness of between 600 MPa and 1,000 MPa. In other implementations, the implant body so formed has a stiffness of between 750 MPa and 850 MPa. In still other implementations, the implant body so formed has a stiffness of between 950 MPa and 1,050 MPa. In additional implementations, the implant body so formed has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

The implant so formed may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
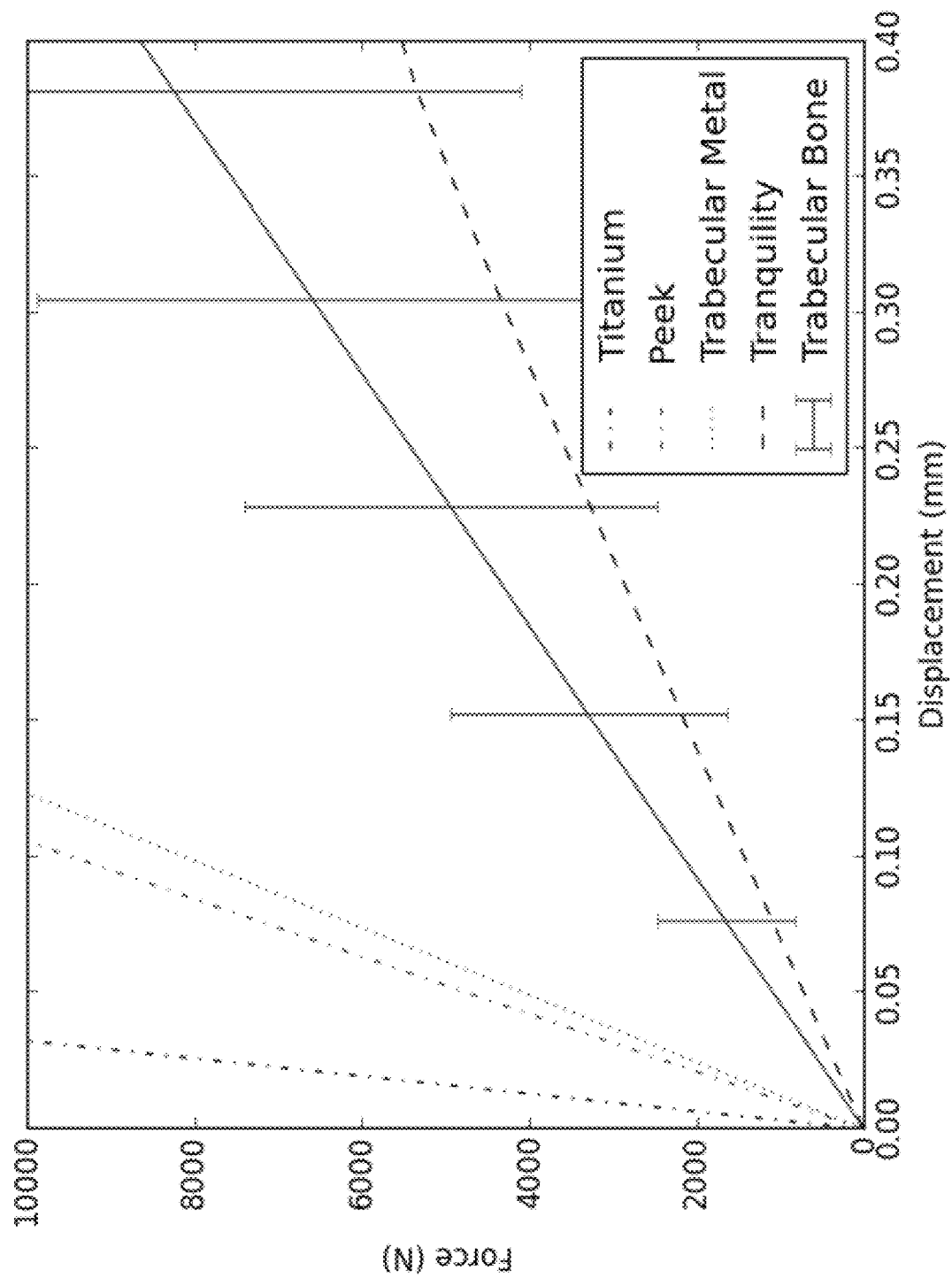
FIG. 1 shows a force-displacement graph of various bulk materials.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide orthopedic implants, particularly implemented in the current examples as interbody spacers, the implants having a combination of correct pore size and stiffness/flexibility. Embodiments of the invention also provide methods for producing such orthopedic implants. When the implants have the proper pore size and stiffness, osteocytes are able to properly bridge the pores of the implant and then experience a proper compressive load to stimulate the bone cells to form bone within the pores throughout the implants according to Wolff's law.

According to embodiments of the invention, an implant includes a body formed of an osteoconductive material. The body may have a stiffness of between 400 megapascals (MPa) and 1,200 MPa. Additionally, the body may include a plurality of pores having an average size of between 150 microns and 600 microns. The pores may be interconnected and permit the growth of bone therein. The implant may be an interbody spacer.

The osteoconductive material may be any of a variety of materials such as titanium, tantalum, and alloys thereof or titanium and alloys thereof such as, for example Ti 6-4 (approximately 6% aluminum, 4% vanadium, up to 0.25% iron, up to 0.2% oxygen and the remainder titanium) and other recognized alloys used for implants. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The implant may be manufactured using an additive manufacturing process. The implant may have a coil spring construction. The coil spring construction may have a vertical spacing between coils of between 250 microns and 350 microns. The coil spring construction may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate embodiments of the invention, an implant includes a body comprising a plurality of coil springs formed of an osteoconductive material. The body may have a stiffness of between 400 MPa and 1,200 MPa. The body may also include a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The implant may be manufactured using an additive manufacturing process. The coil springs of the body may have a vertical spacing between coils of between 250 microns and 350 microns. The coil springs of the body may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate embodiments of the invention, an implant includes a body comprising a plurality of coil springs manufactured using an additive manufacturing process. The coil springs may be arranged into a plurality of overlapping coil packs having coils that are connected and coils that are intertwined without connecting. The coil springs may include coils having a clockwise sweep direction and coils having a counterclockwise sweep direction. The body may have a stiffness of between 400 MPa and 1,200 MPa. The body may have a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

According to further embodiments of the invention, a method of manufacturing an implant includes a step of forming an implant body using an additive manufacturing process. The step of forming an implant body may include forming a plurality of coils of an osteoconductive material. The coils so formed may have a vertical coil spacing and a coil diameter chosen to impart certain physical characteristics to the implant while facilitating use of the additive manufacturing process. The implant body so formed may have a stiffness of between 400 MPa and 1,200 MPa, and may include a plurality of pores having an average size of between 150 microns and 600 microns.

In certain embodiments, the implant body so formed has a stiffness of between 600 MPa and 1,000 MPa. In other embodiments, the implant body so formed has a stiffness of between 750 MPa and 850 MPa. In still other embodiments, the implant body so formed has a stiffness of between 950 MPa and 1,050 MPa. In additional embodiments, the implant body so formed has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

The implant so formed may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

As discussed above, it would be ideal for an implant to provide porosity and stiffness generally similar to actual bone using materials that are conducive to bone growth. In addition to an ideal pore size of 150 microns to 650 microns, an ideal implant would have a stiffness of between 400 MPa and 1.2 gigapascals (GPa) (1,200 MPa). Additionally, when pores are at the larger end of the ideal range, the implant will allow for the fastest and greatest extent of vascularization. Bones that experience larger loads generally have smaller pores and greater stiffness. To grow denser, stronger bone requires an implant with upper-range pore sizes and lower-range stiffness to allow the bone to experience more of the load. In this way, the implant avoids shielding bone within the implant from stress that would cause the bone to grow. Additionally, the larger pores allow the bone to better occupy the available space.

FIG. 1 shows a force-displacement graph of various materials, illustrating the stiffness of the various materials. The line with the steepest slope and thus greatest stiffness is bulk titanium. As shown in FIG. 1, the next stiffest materials are PEEK and trabecular metal (tantalum). In contrast, the stiffness of trabecular bone (shown as exhibiting a range of stiffnesses due to the varying stiffness of different areas of trabecular bone in the body) is still significantly less than even trabecular metal. In contrast, a "tranquility" implant in accordance with embodiments of the invention, though made from titanium or a titanium alloy in this example, achieves a stiffness near the lower end of the stiffness range of trabecular bone. As will be described further below, the exact configuration of coil springs, including coil spacing, etc., in the implant can be varied to achieve varying implant stiffnesses while achieving a desired pore size—something that cannot be achieved with other implant systems.

Figure 2:
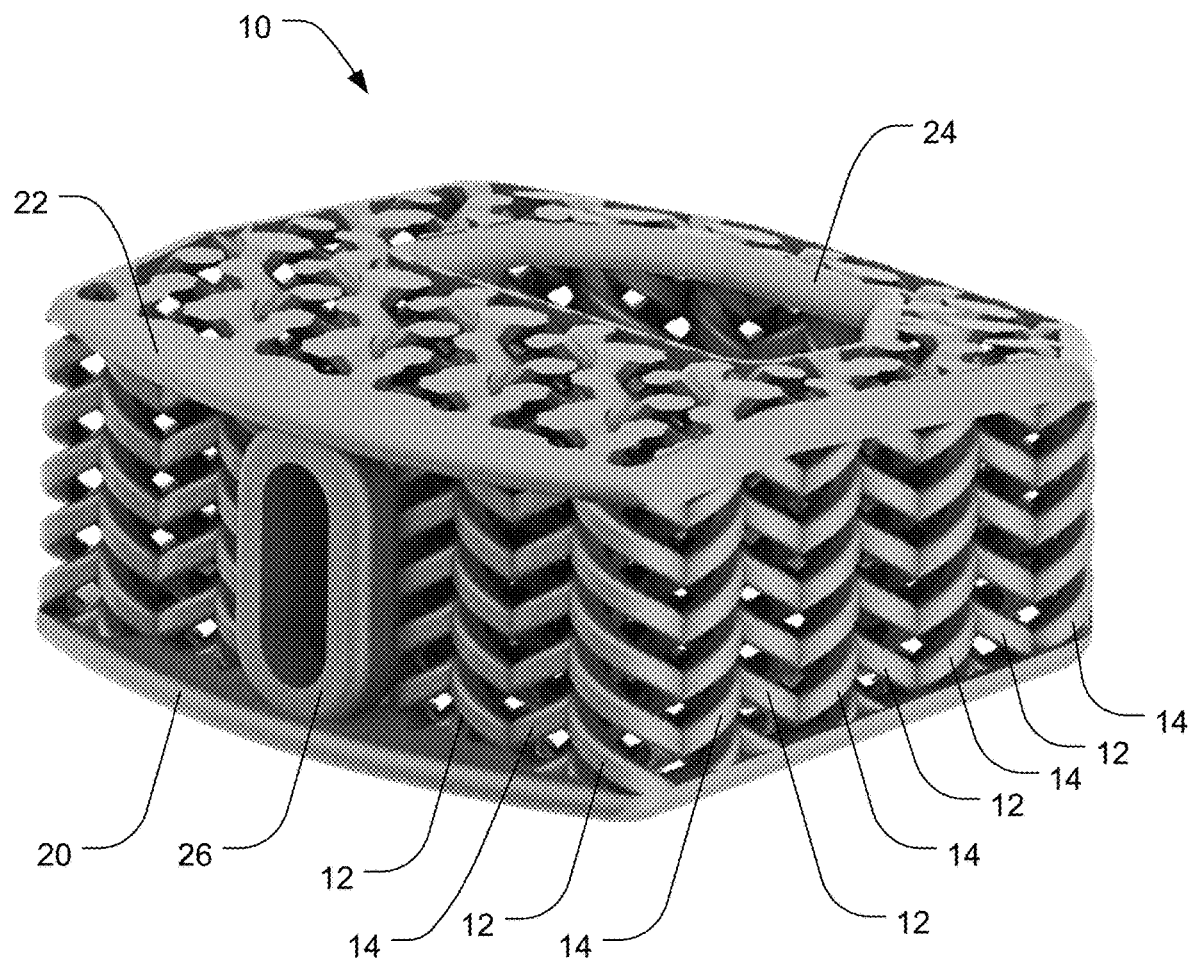
FIG. 2 shows a perspective view of a representative implant.
Figure 3:
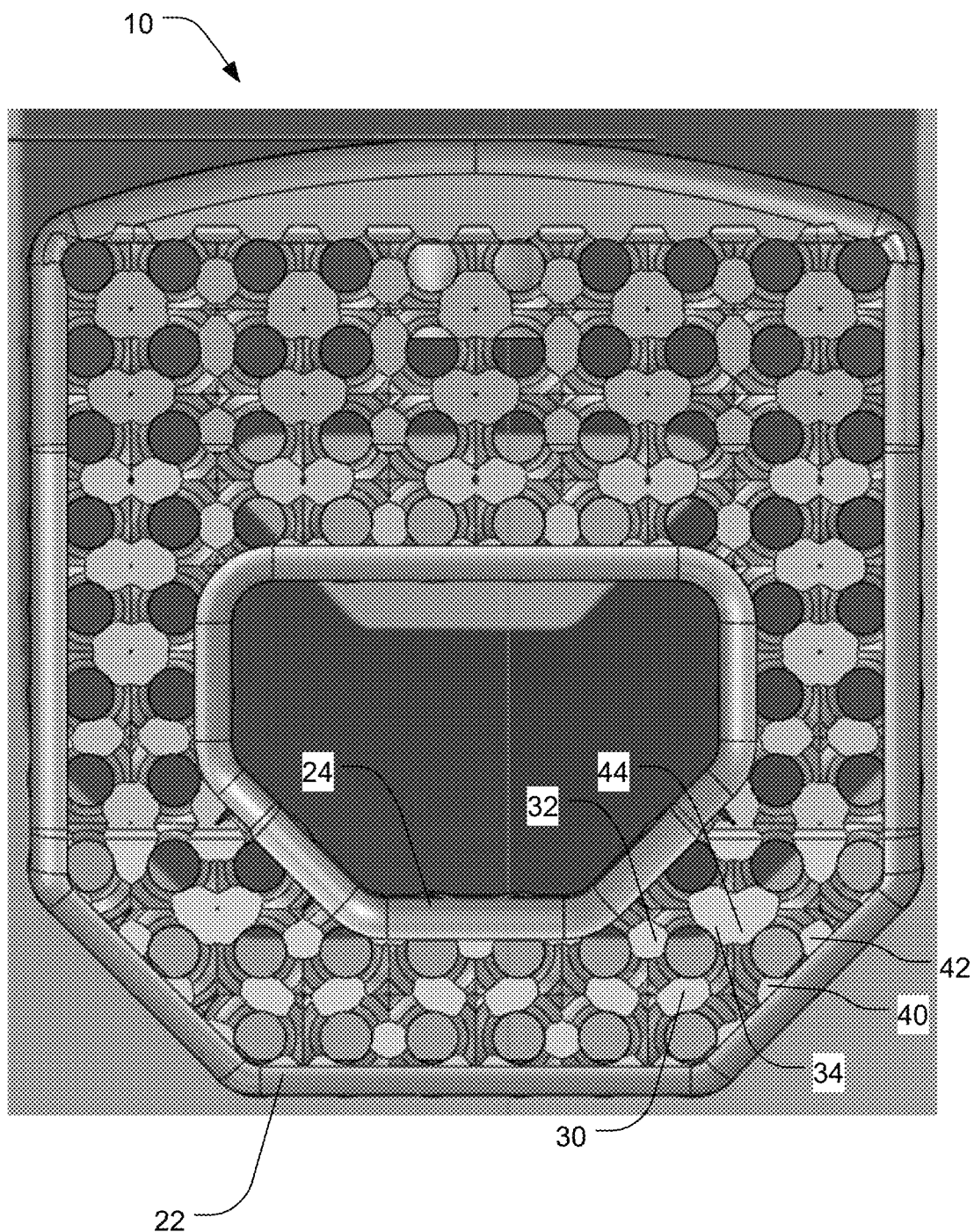
FIG. 3 shows a top view of the implant of FIG. 2.

FIG. 2 shows a perspective view of an illustrative implant 10 demonstrating features in accordance with embodiments of the invention. FIG. 3 shows a top view of the illustrative implant 10. The illustrative implant includes a plurality of two types of coil packs arranged in an alternating arrangement. In the alternating arrangement, a first coil pack 12 having a clockwise sweep direction alternates with a second coil pack 14 having a counterclockwise sweep direction. Each coil pack 12, 14 may be formed of one spring coil or of a plurality of stacked concentric spring coils. In the example shown in FIGS. 2 and 3, each coil pack 12, 14 includes three spring coils.

Figure 4:
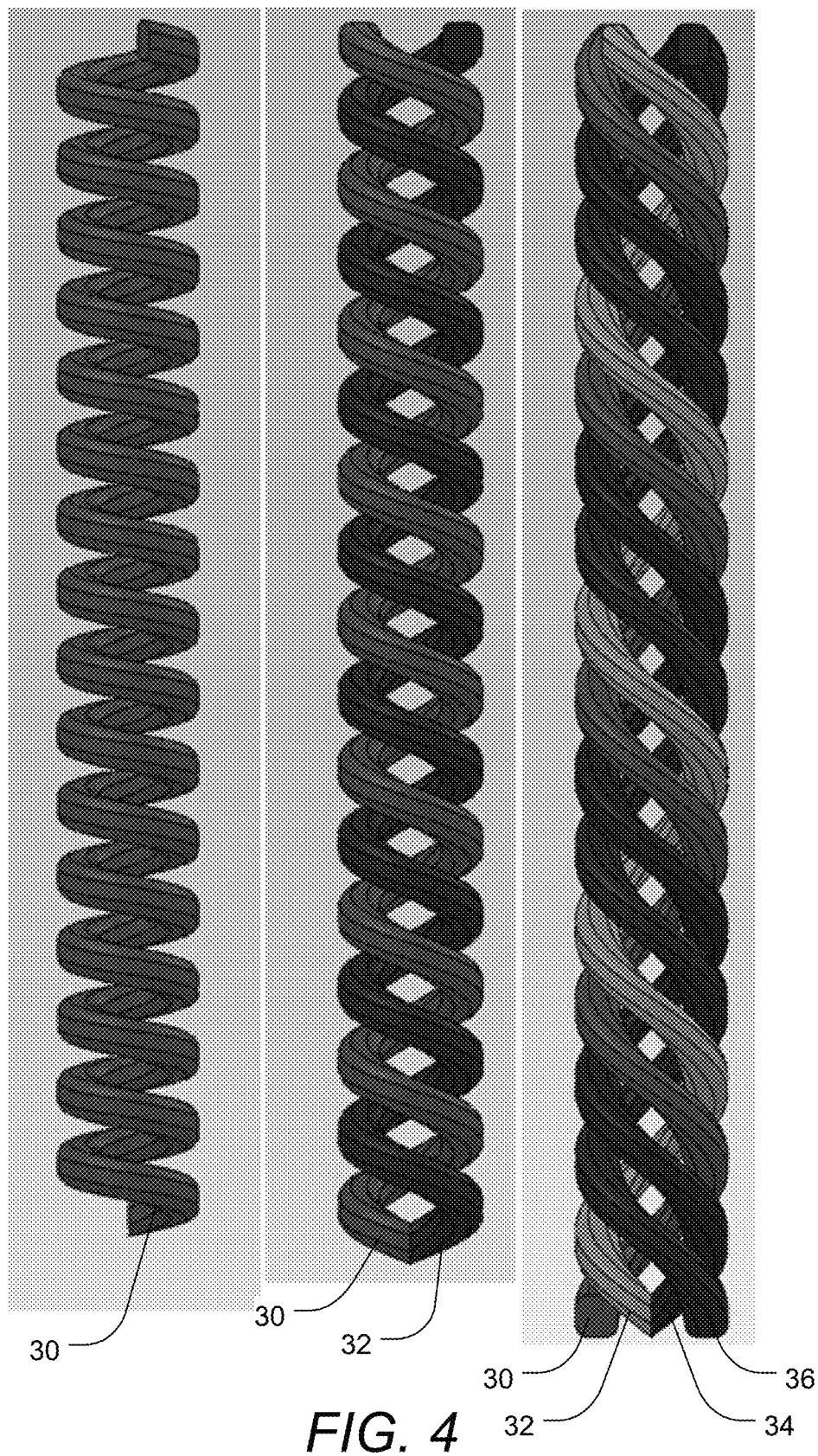
FIG. 4 shows a perspective view of various coil packs for use with implants.

FIG. 4 illustrates how illustrative coil packs may be formed of one or more spring coils. FIG. 4 illustrates three different exemplary coil packs. The left coil pack includes a single spring coil, namely first spring coil 30. The central coil pack includes two spring coils, namely first spring coil 30 and second spring coil 32. In this central example, the spring coils 30, 32 are concentric in that they have a common axis about which each spring coil 30, 32 winds. Each of the spring coils 30, 32 of the central example have a similar wire diameter, coil diameter, and vertical spacing, such that each turn of the coil pack is substantially identical, even though alternating turns of the coil pack are formed from alternating of the first spring coil 30 and the second spring coil 32. Alternatively, if desired, the wire diameter and/or coil diameter of the first spring coil 30 may differ from the wire diameter and/or coil diameter of the second spring coil 32 if desired to impart different stiffness or other characteristics to the implant 10 in which the coil pack is incorporated.

In any coil pack embodiment, the vertical spacing, wire diameter, and/or coil diameter may be varied as desired to vary the stiffness and other characteristics of the implant 10 in which the coil pack is incorporated. For example, in comparing the left coil pack of FIG. 4 to the middle coil pack of FIG. 4, it may be seen that the total number of wire turns in each example is similar, even though the turns of the central example are split between two spring coils while the turns of the left example are formed from a single spring coil. In each example of FIG. 4, the wire diameter and coil diameter is similar. The stiffness of each example is varied by the differing coil pitches achieved by having two spring coils as opposed to a single spring coil.

FIG. 4 includes a third example of a coil pack on the right side. This example is formed of four spring coils, namely first spring coil 30, second spring coil 32, third spring coil 34, and fourth spring coil 36. This example further illustrates that the number of spring coils forming each spring pack may be varied as desired, and it will be a matter of straightforward experimentation with varied numbers of spring coils, spring wire thickness, and vertical coil spacing to achieve a desired stiffness of each coil pack. In each of the coil packs of FIG. 4, the spring coils (and the coil packs themselves) have a clockwise sweep direction. Essentially identical coil packs may be formed having counter-clockwise sweep direction, even though such are not illustrated in FIG. 4.

Figure 5:
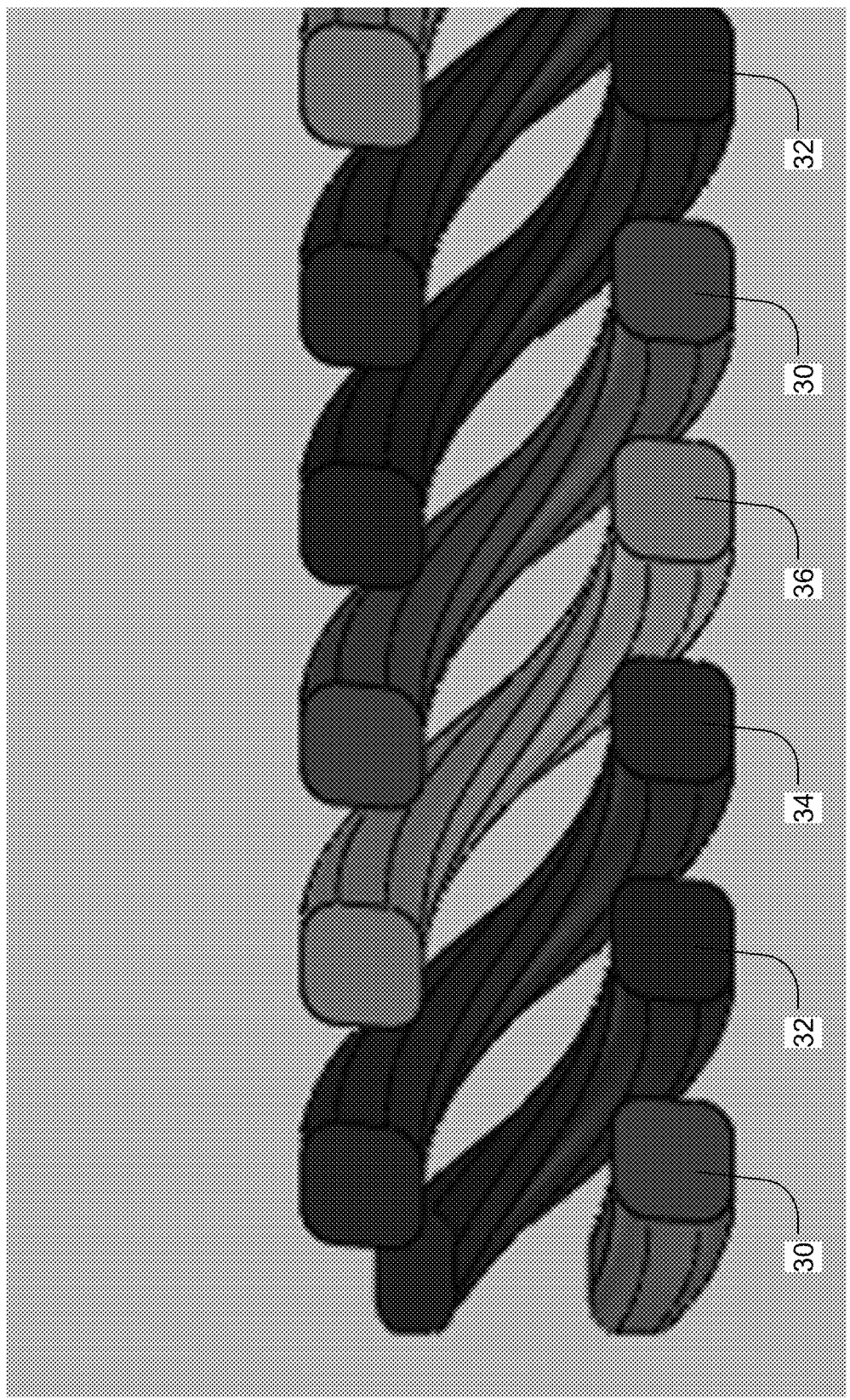
FIG. 5 shows a cross-sectional view of an illustrative coil pack.
Figure 7:
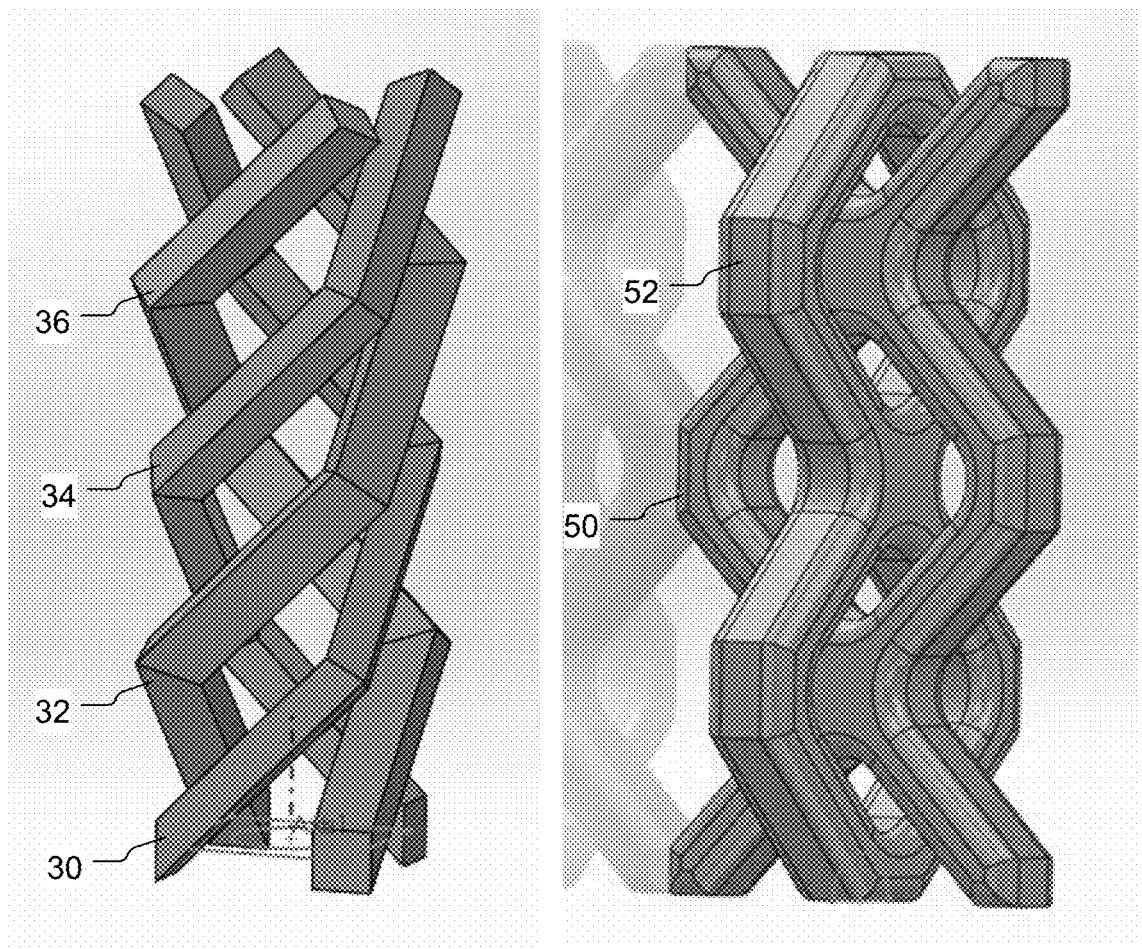
FIG. 7 shows a perspective view of illustrative alternate coil packs.

The spring coils of each coil pack may assume any desired cross-sectional shape. For example, FIG. 5 shows a cross-sectional view of a four-wire coil pack formed of first spring coil 30, second spring coil 32, third spring coil 34, and fourth spring coil 36. In this example, the wire of each spring coil has a square cross-sectional shape with radiused edges, but essentially any cross-sectional shape may be used. For example, the spring coils may have a round cross-sectional shape, an elliptical cross-sectional shape, a square cross-sectional shape, a rectangular cross-sectional shape, or a cross-sectional shape of any desired number of sides (pentagonal, octagonal, etc.), with or without rounded or radiused edges. Further examples of illustrative shapes and configurations of spring coils and coil packs are shown in FIG. 7, as discussed below.

The coil pack or swept coil of each coil pack has a stiffness and strength that depends on the base diameter of the coil pack, which can be chosen to facilitate bone growth. The stiffness and strength are also dependent on the pitch of the coils in the coil pack, which can further be chosen to facilitate bone growth by defining a proper size space between coils. The stiffness and strength are also dependent on the wire diameter and modulus of rigidity of the chosen material. When coils are placed together to form coil packs, the needed pore spacing for bone growth is created while the bulk strength is increased and the bulk stiffness of the device is decreased.

Forming the body of the implant 10 as coil packs 12, 14 allows an additive manufacturing process to be used with traditionally biocompatible and osteoconductive materials (e.g. titanium and alloys thereof) while still maintaining a desired stiffness. Additionally, this type of construction allows the additive manufacturing process to be used while still achieving the desired pore size. Traditionally, additive manufacturing processes were incapable of being used to provide the desired pore size. Specifically, the pores of prior devices were conceived in negative, thus limiting the pore size to the minimum feature size of the additive manufacturing process, which in turn determines the bulk stiffness (typically much higher than the stiffness of trabecular bone).

Using the coil pack construction discussed herein allows for the creation of pores by stacking overlapping geometry. In effect, the overlapping geometry allows the pore size to be smaller and better shaped without reducing the minimum feature size of the additive manufacturing process. While the smaller pore size achieved in this way would traditionally increase stiffness, the clever geometry of the coil packs allows the bulk flexibility to be increased as governed by the following equation:

$$T = \frac{J_T}{r}\tau = \frac{J_T}{\ell}G\theta$$

In this way, the implant 10 may have a micro-porous structure effectively formed of flexible micro struts that in concert decrease the bulk stiffness of the device, allowing for use of osteoconductive materials such as Ti 6-4, tantalum, or other alloys of titanium or tantalum. The pore size thus achieved is large enough for vascularization and rapid bone growth, and not too large for bone bridging, and the bone is able to grow both on and throughout the device. The contact area between the device and the bone can be increased, mitigating overloading of local bone at the bone-to-device interface.

As illustrated in FIGS. 2 and 3, the coil packs 12, 14 may be arranged in a way so as to overlap/intersect. This overlapping/intersecting of clockwise and counter-clockwise sweeping coil packs is illustrated in more detail in FIG. 6. In this Figure, a full set of coil packs is shown at the left, and the right shows what may either be an entire set of coil packs, or merely a single set of spring coils from the coil pack at the left of FIG. 6. In the left illustrated example of FIG. 6, the first coil pack 12 has four individual spring coils, namely, first spring coil 30, second spring coil 32, third spring coil 34 and fourth spring coil 36, all having a clockwise sweep direction, while the second coil pack 14 has three individual spring coils, namely, first spring coil 40, second spring coil 42, and third spring coil 44. Thus, the first coil pack 12 has an additional spring coil, fourth spring coil 36 that is unpaired and has no corresponding spring coil in the second coil pack 14. This may be by design to decrease stiffness of the implant 10 containing the joined coil packs 12, 14.

Figure 6:
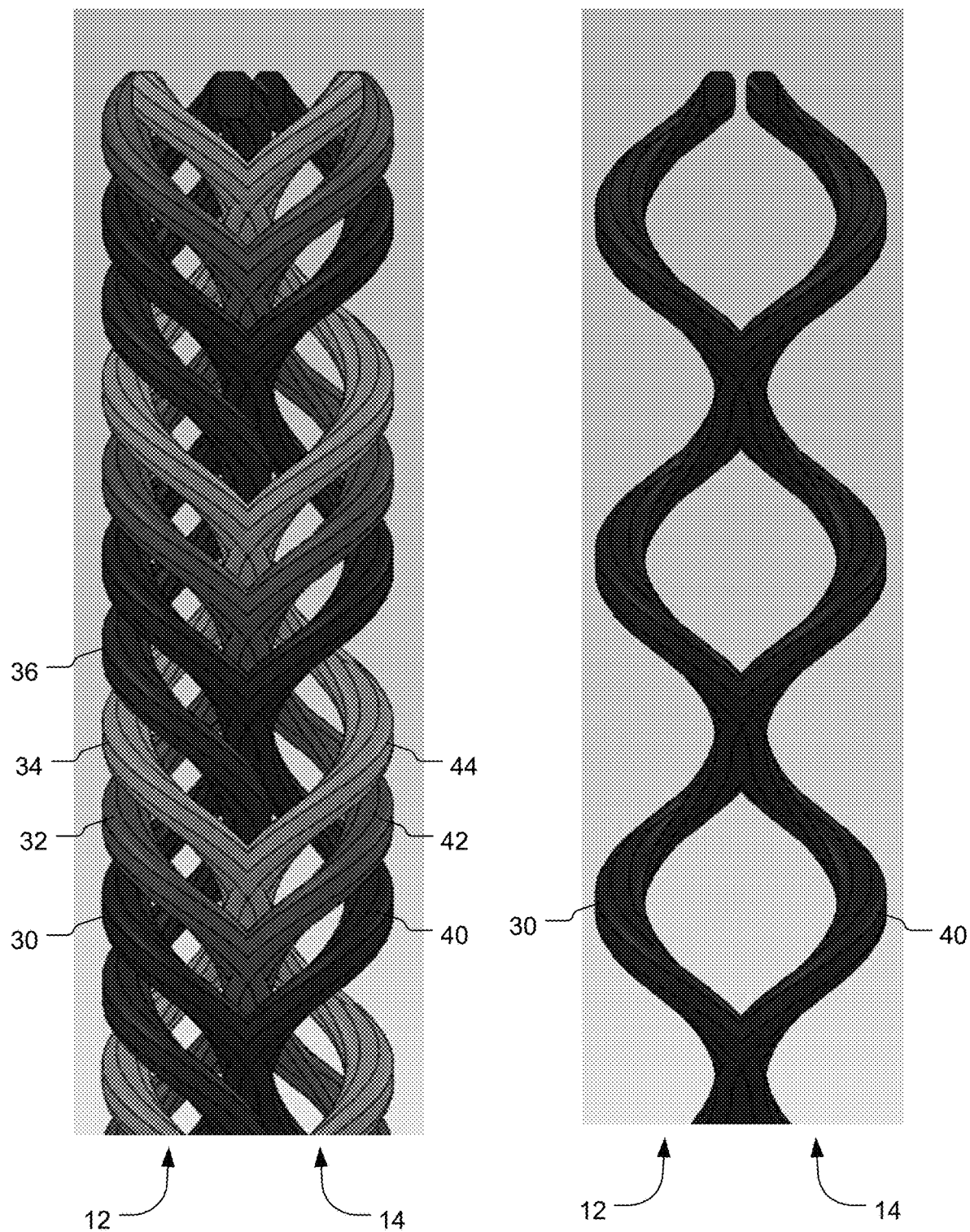
FIG. 6 shows a perspective view of illustrative adjacent coil packs having clockwise and counter-clockwise sweep directions.

As may be seen in FIG. 16, and particularly in the single-spring-coil example at the right of FIG. 6, the individual spring coils of each coil pack 12, 14 may be unitarily formed or joined at their points of intersection. As the implant 10 is formed in the additive manufacturing process, the individual coils of the coil pack are unitarily formed such that while the coils of the coil packs may be conceptually viewed as separate coils, they are actually united in a way that provides a measure of overall structure to the implant 10. Additionally, this construction overcomes limitations of the additive manufacturing process, allowing for creation of the ideal pore size. This type of construction effectively avoids the additive manufacturing process's limitations, as the additive manufacturing process views each spring coil as an independent structure. The overlapping coil packs have the added advantages of tailored shear stiffness and strength as well as load sharing between adjacent coil packs.

The top view of the implant 10 shown in FIG. 3 illustrates how the coils of adjacent coil packs are joined at one cross-sectional point, namely, the top surface of the implant 10. In this Figure, the third spring coil 34 of one of the first coil packs 12 is joined to the third spring coil 44 of one of the second coil packs 14. The second spring coil 32 of that first coil pack 12 is joined to the second spring coil 42 of a different second coil pack 14, and the first spring coil 30 of that first coil pack 12 is joined to the first spring coil 40 of yet another different second coil pack 14. Thus each coil pack 12, 14 is unitarily formed on all sides to the coil packs 14, 12 adjacent to them, respectively, forming the implant 10 as a unitary, though relatively flexible body.

If desired, the implant 10 may include some areas of additional structure, rigidity, and strength at locations where the normal increased flexibility is not needed or is not desired. For example, the implant 10 shown in FIGS. 2 and 3 may include an outer bottom rim 20, an inner bottom rim (not shown) an outer top rim 22, and an inner top rim 24. The inner top rim 24 and the inner bottom rim may define top and bottom edges of a void adapted to receive a bone graft material such as morcellized bone (living bone) prior to implantation of the implant 10, thereby providing a seed to better initiate bone growth into the implant 10 after implantation, as is known in the art. Additionally, the implant 10 may include a rigid strut 26 formed on one side of the implant 10, if it is determined that the implant 10 should be more rigid on one side thereof.

As discussed above, the cross-sectional form of each coil spring may be varied, and the configuration of the coil packs may also take other forms as long as they achieve the purposes discussed herein. To this end, FIG. 7 illustrates alternate embodiments of coil packs that could be used with embodiments of the implant 10. The left coil pack of FIG. 7 includes first spring coil 30, second spring coil 32, third spring coil 34, and fourth spring coil 36, as did one of the examples of FIG. 4. In this example, however, the spring coils 30, 32, 34, and 36 have a non-rounded square cross-sectional profile.

In the right coil pack of FIG. 7, the coil pack includes a first diamond structure 50 and a second diamond structure 52, illustrating that the coil packs need not be formed solely of standard sweep coils, but that coil packs may be formed of any microstructure that is capable of being manufactured using an additive manufacturing process while providing a proper pore size and bulk stiffness. The interlocking diamond shape of the right coil pack of FIG. 7 achieves this in a different fashion than the coil packs illustrated and discussed previously, but still provides an interlocking structure and a known small pore size within the constraints of existing additive manufacturing processes.

The illustrated implant embodiment of FIGS. 2 and 3 is an interbody spacer aimed at facilitating bony fusion of adjacent segments of the spine. The implant 10 can be placed in an intervertebral space to provide support to the spine during bone growth, but furthermore can work to promote and stimulate bone growth. Unlike prior devices, the implant 10 can simultaneously promote and stimulate bone growth throughout the device (not just onto the surface of the device) while maintaining stable support.

It is envisioned that the systems and methods illustrated herein may be useful in other types of orthopedic implants, and that the stiffness and pore sizes may be modified as appropriate to achieve the desired characteristics at the location where such implants are to be used.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. An implant comprising:
    a body comprising a biocompatible material, the body further comprising:
        a caudal surface configured to contact a first bony endplate of a patient's spine;
        a cranial surface configured to contact a second bony endplate of the patient's spine;
        a porous structure disposed between the caudal surface and the cranial surface, the porous structure being configured to be open to at least one of the first bony endplate and the second bony endplate; and
        a structural element having a different configuration than the porous structure, the structural element being coupled to the porous structure, the structural element comprising a first band surrounding a first perimeter of the body and a second band surrounding a second perimeter of the body,
    wherein the porous structure comprises a strand that causes the porous structure to define a plurality of pores.

2. The implant as recited in claim 1, wherein the first perimeter comprises an outermost perimeter of the implant, and wherein the strand is coupled to the first band and to the second band.

3. The implant as recited in claim 1, wherein the porous structure comprises a coil pack comprising the strand.

4. The implant as recited in claim 3, wherein a longitudinal axis of the coil pack is oriented along an axis of compression when a load is placed on the cranial surface.

5. The implant as recited in claim 4, wherein a longitudinal axis of the strand is oriented closer to orthogonal than to parallel to the longitudinal axis of the coil pack.

6. The implant as recited in claim 5, wherein a first portion of the strand is configured to move toward a second portion of the strand in response to the load placed on the cranial surface, thereby compressing the coil pack.

7. The implant as recited in claim 1, wherein at least one of the first band and the second band is contiguous.

8. The implant as recited in claim 1, wherein the body of the implant has a stiffness of less than 1,200 megapascals.

9. The implant as recited in claim 1, wherein the strand comprises a first terminus, a second terminus, and a middle portion disposed between the first terminus and the second terminus, and wherein each of the first terminus, the second terminus, and the middle portion is entirely positioned in a ventral half of the implant.

10. The implant as recited in claim 1, wherein at least one of the first band and the second band is disposed at the cranial surface.

11. The implant as recited in claim 10, wherein the second band is disposed in a caudal half of the implant.

12. An interbody spacer implant comprising:
    a body comprising:
        a caudal surface configured to contact a first bony endplate of a patient's spine;

a cranial surface configured to contact a second bony endplate of the patient's spine; and a porous structure disposed between the caudal surface and the cranial surface, wherein:

the porous structure comprises a coil pack configured to be open to at least one of the first bony endplate and the second bony endplate and defining a plurality of pores, and a long axis of the coil pack is closer to parallel than to orthogonal to a compressive load when the compressive load is applied to at least one of the cranial surface and the caudal surface.

13. An interbody spacer implant comprising:

a body comprising:

a caudal surface configured to contact a first bony endplate of a patient's spine;

a cranial surface configured to contact a second bony endplate of the patient's spine; and a porous structure disposed between the caudal surface and the cranial surface, wherein the porous structure comprises a strand that causes the porous structure to define a plurality of pores, wherein a cross-sectional diameter of the strand is solid throughout, and wherein a terminus of the strand extends to an external surface of the body, and wherein the plurality of pores is configured to be open to at least one of the first bony endplate and the second bony endplate.

14. The interbody spacer implant of claim 13, wherein the terminus of the strand extends to the cranial surface.

15. The interbody spacer implant of claim 14, wherein an opposing terminus of the strand extends to the caudal surface.

16. An interbody spacer implant comprising:

a body comprising a porous structure;

a cranial surface having a cranial structural portion; and a caudal surface that is spaced apart from the cranial surface, the caudal surface having a caudal structural portion;

wherein:

the porous structure is disposed between the cranial surface and the caudal surface;

the cranial surface is configured to contact a first segment of bone;

the caudal surface is configured to contact a second segment of bone;

a cranial portion of the porous structure is configured to be open to the first segment of bone;

a caudal portion of the porous structure is configured to be open to the second segment of bone; and the cranial structural portion and the caudal structural portion each have different configurations than the body, such that a stiffness of the cranial structural portion and a stiffness of the caudal structural portion are each different than a stiffness of the body.

17. The interbody spacer implant of claim 16, wherein the porous structure comprises a first strand and a second strand, and wherein at least one of the cranial structural portion and the caudal structural portion couples the first strand to the second strand.

18. The interbody spacer implant of claim 17, wherein the porous structure comprises a lattice structure comprising a pore size of between 150 microns and 650 microns.

19. An interbody spacer implant comprising:

a body comprising a biocompatible material, the body further comprising:

a caudal surface configured to contact a first bony endplate of a patient's spine;

a cranial surface configured to contact a second bony endplate of the patient's spine; and a porous structure extending between the caudal surface and the cranial surface, wherein the porous structure is configured to be open to at least one of the first bony endplate of the patient's spine and the second bony endplate of the patient's spine, wherein the porous structure comprises a flexible element defining a plurality of pores, and wherein the porous structure is sufficiently flexible such that the interbody spacer implant has a compression stiffness of between 0.3 GPa and 4.0 GPa.

20. The interbody spacer implant of claim 19, wherein the porous structure comprises a coil pack comprising the flexible element, and wherein the porous structure comprises pores from 150 microns to 650 microns in size.

\* \* \* \* \*